United States Patent
Paul et al.

(10) Patent No.: US 6,346,650 B1
(45) Date of Patent: Feb. 12, 2002

(54) METHOD FOR MAKING MIXED HIGH PURITY (METH)ACRYLIC ANHYDRIDES

(75) Inventors: Jean-Michel Paul, Metz; Alain Riondel, Forbach; Frédéric Fabis, Caen; Sylvain Rault, Moult, all of (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/601,240

(22) PCT Filed: Jan. 28, 1999

(86) PCT No.: PCT/FR99/00164

§ 371 Date: Jul. 31, 2000

§ 102(e) Date: Jul. 31, 2000

(87) PCT Pub. No.: WO99/38837

PCT Pub. Date: Aug. 5, 1999

(30) Foreign Application Priority Data

Feb. 2, 1998 (FR) ............................................. 98 01155

(51) Int. Cl.[7] .............................................. C07C 51/56
(52) U.S. Cl. ....................................... 562/894; 562/888
(58) Field of Search ................................. 562/888, 894

(56) References Cited

U.S. PATENT DOCUMENTS 3,718,675 A 2/1973 Tesoro

OTHER PUBLICATIONS

Hwa et al, Acrylic Anhydrides and Polymers Derived Therefrom, Journal of Polymer Science: Part A, vol. 2 p. 2386 (1961).*

\* cited by examiner

*Primary Examiner*—Gary Geist
*Assistant Examiner*—Robert W. Deemie
(74) *Attorney, Agent, or Firm*—Millen, White, Zelano & Branigan, P.C.

(57) ABSTRACT

The invention concerns a method consisting in making a mixed (meth)acrylic anhydride of formula (I) by reacting an alkaline (meth)acrylate of formula (II) and a chloroformate of formula (III), carrying out said reaction in an aqueous medium and in the absence of amines, the mol ratio chloroformate (III)/alkaline (meth)acrylate (II) being at least equal to 1.15. $R^1$ represents H or $CH_3$; $R^2$ represents an alkyl, alkenyl, aryl, alkaryl or aralkyl residue; and M is an alkaline metal.

20 Claims, No Drawings

METHOD FOR MAKING MIXED HIGH PURITY (METH)ACRYLIC ANHYDRIDES

The present invention relates to a process for manufacturing mixed anhydrides represented by the general formula (I):

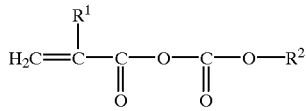
(I)

in which:
R$^1$ represents H or CH$_3$; and
R$^2$ represents an alkyl, alkenyl, aryl, alkaryl or aralkyl residue, according to which process an alkali metal (meth)acrylate of general formula (II):

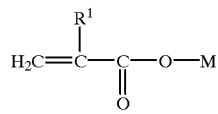
(II)

in which:
R$^1$ is as defined above; and
M is an alkali metal, is reacted with a chloroformate of general formula (III):

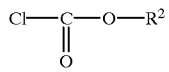
(III)

in which R$^2$ is as defined above.

Mixed anhydrides are mild acylating agents, the use of which has been described in peptide synthesis in place of conventional anhydrides

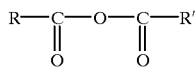

and acid chlorides

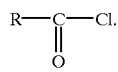

In audition, the only by-products generated by the mixed anhydrides of formula (I) in the acylation reactions are CO$_2$ and the alcohol R$^2$OH, which are easier to remove than (meth)acrylic acid or HCl.

The processes for synthesizing the non-acrylic mixed anhydrides which have been described in the literature are mostly based on the method described by Vaughan in J. Am. Chem. Soc. 73, 3547, 1951: the mixed anhydride is synthesized by equimolar reaction between an alkyl chloroformate and a tertiary amine carboxylate, at low temperature (generally less than 0°), in a solvent medium (tetrahydrofuran, acetone, toluene, chloroform, etc.). Besides the need to work in a solvent medium, at very low temperature, one of the main constraints of the process lies in the fact that it is necessary to separate off by filtration the trialkylammonium chloride which precipitates in the medium.

In Bull. Chem. Soc. Jap. 1968, 41, 2521-3, Harada and Kondo describe, among the examples, the synthesis of carboethoxymethacrylic anhydride:

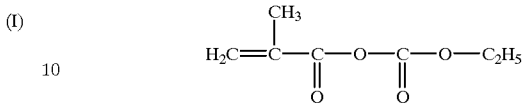

by reaction between potassium methacrylate and ethyl chloroformate, in a solvent medium (chloroform), at 0° C., in the presence of pyridine.

The synthesis of carboethoxymethacrylic anhydride is also described in French patent application FR-A-2 212 340, starting with triethyl-ammonium methacrylate and ethyl chloroformate in a solvent medium (acetonitrile).

The synthesis of non-acrylic mixed anhydrides is described in German patent DE-C-1 133 727 by reaction between a carboxylate and a chloroformate in a chloroformate/carboxylate molar ratio of between 0.95 and 1.10.

The processes described in the literature mostly relate to non-acrylic mixed anhydrides and present, depending on the case, many drawbacks, the chief ones being the use of solvents and the use of amines in stoichiometric amount relative to the carboxylic acid or in catalytic amount. The need to separate out the alkylammonium chloride by filtration also constitutes a drawback.

In most of the processes described in the literature, the reagents (II) and (III) are used in equimolar proportions or between 0.95 and 1.1. Under these conditions, it is possible to obtain a mixed (meth)acrylic anhydride

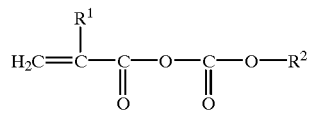

containing little symmetrical anhydride

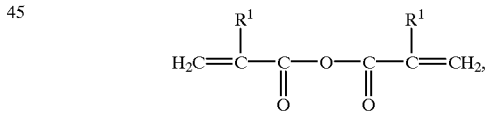

R$^1$ being as defined above. This is particularly inconvenient when it is desired to synthesize carboxyalkoxy (meth)acrylic anhydride containing very little methacrylic anhydride.

It has been discovered, surprisingly, that these problems can be solved by modifying the conditions of the reaction between compounds (II) and (III), and in particular by carrying out this synthesis with a compound (III)/compound (II) molar ratio of greater than or equal to 1.15.

A subject of the present invention is thus a process for preparing a high-purity mixed (meth)acrylic anhydride (I), by reaction between the abovementioned compounds (II) and (III), characterized in that the said reaction is carried out in an aqueous medium and in the absence of amines, the chloroformate (III)/alkali metal (meth)acrylate (II) molar ratio being at least equal to 1.15.

In general, the reaction is carried out with compounds (II) and (III) in which:

$R^2$ is chosen from $C_1-C_{40}$ alkyl, $C_2-C_{40}$ alkenyl, phenyl, phenyl ($C_1-C_{40}$ alkyl) and ($C_1-C_{40}$ alkyl) phenyl residues; and M represents Na or K.

The mixed anhydrides of formula (I) in which $R^2$ represents $C_1-C_{40}$ alkyl, such as ethyl, n-propyl, isopropyl, n-butyl or isobutyl, are of particular interest and constitute a family of preferred mixed anhydrides of the invention. These are mild acylating agents which can very advantageously replace methacrylic anhydride or (meth)acryloyl chloride which generate methacrylic acid or hydrochloric acid in acylation reactions.

In the process of the present invention, the chloroformate (III)/alkali metal (meth)acrylate (II) molar ratio can be between 1.15 and 2, preferably between 1.5 and 1.7, in order to limit the formation of by-products of the type

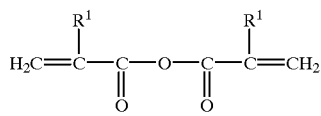

for example. At and above 1.15, a substantial improvement in the selectivity and yields are observed; thus, when the synthesis of carboethoxymethacrylic anhydride is carried out by reaction between sodium methacrylate and ethyl chloroformate, a reduction in the formation of methacrylic anhydride and by-products is observed. Moreover, a high molar ratio is favourable in terms of selectivity, but is penalizing with respect to the production efficiency.

The reaction according to the present invention is advantageously carried out at a temperature of between −10 and +30° C., preferably between +10 and +20° C.

In accordance with one specific embodiment of the present invention, the alkali metal (meth)acrylate (II) is prepared in aqueous solution by neutralizing (meth)acrylic acid with the hydroxide MOH, the MOH/(meth)acrylic acid molar ratio being between 1 and 1.5, in particular between 1 and 1.1, and the water/alkali metal (meth)acrylate (II) weight ratio being between 1.5 and 7, in particular between 1.5 and 2, after which the chloroformate (III) is reacted with the alkali metal (meth)acrylate (II).

In accordance with one particularly advantageous characteristic of the present invention, the reaction between the alkali metal (meth)acrylate (II) and the chloroformate (III) is carried out in the presence of a phase-transfer catalyst, dissolved or fixed to a polymeric support such as a styrene-divinylbenzene copolymer or a crosslinked polyvinylpyridine resin and used in particular in a proportion of from 0.001 to 0.02 mol, in particular from 0.005 to 0.01 mol, per mole of alkali metal (meth)acrylate (II).

The phase-transfer catalyst is advantageously chosen from quaternary ammonium salts, phosphonium salts and crown ethers.

As examples of quaternary ammonium salts

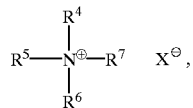

mention may be made of those in which:

$R^4$ to $R^7$ each represent $C_1-C_{40}$ alkyl, such as $CH_3$, $C_2H_5$, $C_4H_9$, $C_8H_{17}$ and $C_{16}H_{33}$, or aryl such as phenyl, or aralkyl such as benzyl;

X represents one from among Cl, Br, I, OH and $HSO_4$;

and, in particular, tetramethylammonium chloride, benzyltrimethylammonium chloride, benzyltri-n-butylammonium chloride, tetra-n-butylammonium chloride, tetra-n-butylammonium bromide, methyltrioctylammonium bromide and tetra-n-butyl-ammonium hydrogen sulphate;

as examples of phosphonium salts, mention may be made of $(C_4H_9)_4P^\oplus Cl^\ominus$, $(C_4H_9)_4P^\oplus Br^\ominus$, $(C_8H_{17})_3 C_2H_5P^\oplus Cl^\ominus$, $(C_4H_9)_3C_6H_5P^\oplus Cl^\ominus$; and as examples of crown ethers, mention may be made of 18-crown-6 and dibenzoyl-18-crown-6.

Working in the presence of a phase-transfer catalyst increases the reaction substantially (3 to 5 hours as opposed to 15 hours without catalyst).

The reaction according to the invention is generally carried out with stirring in a thermostatically-controlled jacketed reactor while rigorously controlling the temperature. The crude reaction mixture separates out into two phases by settling if the stirring is stopped (or into three phases if a phase-transfer catalyst is used, fixed to a polymeric support). The reaction progress is monitored by regularly taking samples of the aqueous phase and assaying the residual alkali metal (meth)acrylate (II). The reaction is considered as complete when the degree of conversion of the alkali metal (meth)acrylate (II) is greater than 95%.

At the end of the reaction, the phases of the two-phase or three-phase reaction mixture are separated by settling at room temperature, advantageously washed with water (amount: 20 to 100% of the weight of the organic phase, preferentially 30 to 40%) at room temperature, the organic phase containing the mixed anhydride (I) and the excess chloroformate (III) then being stripped off under vacuum at a temperature of less than or equal to 35° C. The mixed anhydride is thus obtained in very high purity.

It is necessary to introduce at least one polymerization inhibitor into the reaction medium, in a proportion of from 500 to 5000 ppm, in particular from 500 to 1000 ppm, relative to the alkali metal (meth)acrylate (II)—or to its precursor (meth)acrylic acid—in order to overstabilize the latter.

As examples of polymerization inhibitors, mention may be made of hydroquinone methyl ether, hydroquinone, phenothiazine and di-tert-butyl-para-cresol.

The examples which follow illustrate the present invention without, however, limiting its scope. In these examples, the percentages are given on a weight basis except where otherwise indicated.

EXAMPLE 1

408 g of an aqueous 26.5% sodium methacrylate solution, into which are introduced 900 mg of hydroquinone methyl ether, are introduced into a jacketed reactor whose temperature is maintained with the aid of a circulation of water thermostatically adjusted to 20° C.; next, 162.8 g of ethyl chloroformate (ethyl chloroformate/sodium methacrylate molar ratio: 1.5:1) are introduced over 5 minutes.

The heterogeneous mixture is stirred for 15 hours. The phases are then separated by settling at room temperature. The organic phase is dried over calcium sulphate and the volatiles are then stripped off under vacuum at a temperature of less than 35° C., in order to remove the excess chloroformate.

153 g of product are thus obtained (yield: 96.7%) in a carboethoxymethacrylic anhydride NMR purity of 95%, the remaining 5% consisting of methacrylic

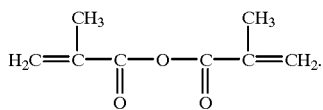

EXAMPLES 2 TO 5

Example 1 is repeated, modifying the temperature and the ethyl chloroformate/sodium methacrylate molar ratio.

The results are reported in Table 1.

TABLE 1

| Example | 2 | 3 | 4 | 5 |
|---|---|---|---|---|
| Ethyl chloroformate/sodium methacrylate molar ratio | 1.5 | 1.5 | 1.5 | 3 |
| Temperature (° C.) | 5 | 25 | 35 | 15 |
| Reaction time (h) | 30 | 8 | 7 | 24 |
| Degree of conversion of the sodium methacrylate (%) | 81 | 90.3 | 97.4 | 98.5 |
| Composition of the organic phase separated out by settling (% by weight) | | | | |
| ethyl chloroformate | 39.7 | 29 | 22.5 | 63 |
| carboethoxymethacrylic anhydride | 55 | 63 | 65 | 35 |
| methacrylic anhydride | 5 | 7 | 11 | 2 |
| ethanol | <1 | <1 | 1 | |
| water | 0.3 | 0.2 | 0.1 | |
| Composition of the organic phase stripped of volatiles (% by weight) | | | | |
| carboethoxymethacrylic anhydride | 91 | 90 | 85.5 | 94.5 |
| methacrylic anhydride | 9 | 10 | 14.5 | 5.5 |

EXAMPLE 6

The process is performed in the same apparatus as in Example 1.

445.1 g of aqueous 33.2% sodium methacrylate solution stabilized with 1.2 g of hydroquinone methyl ether are loaded in. 8.8 g of tetra-n-butylammonium bromide (0.02 mol/mole of sodium methacrylate) are then introduced. Next, 193.2 g of ethyl chloroformate are introduced with stirring and while maintaining the temperature of the medium at 20° C. (ethyl chloroformate/sodium methacrylate molar ratio =1.3).

The reaction mixture is left stirring while controlling the temperature at 20° C. The reaction progress is monitored by assaying the residual sodium methacrylate in the aqueous phase separated out by settling (the phases of the mixture separate out by settling as soon as the stirring is stopped). After reaction for 3 hours, the degree of conversion of the sodium methacrylate is greater than 99%. The reactor is then emptied, the phases of the reaction mixture are separated by settling at room temperature, the organic phase is washed with 57 g of water and the washed organic phase is separated out by settling.

234.5 g of crude washed product are thus recovered, which product is stabilized with 0.02 g of di-tert-butyl-para-cresol. The excess chloroformate is removed under vacuum using a rotary evaporator at a temperature of less than 35° C.

198 g of carboethoxymethacrylic anhydride are obtained, the NMR purity of which is indicated, with the yield, in Table 2 below.

EXAMPLES 7, 8 (COMPARATIVE) AND 9 (COMPARATIVE)

Example 6 is repeated, varying the ethyl chloroformate/sodium methacrylate molar ratio.

The results are reported in Table 2.

TABLE 2

| EXAMPLE | 6 | 7 | 8 (comp.) | 9 (comp.) |
|---|---|---|---|---|
| Ethyl chloroformate/sodium methacrylate molar ratio | 1.3 | 1.15 | 1.05 | 1.1 |
| Composition of the final product (% by weight) | | | | |
| carboethoxymethacrylic anhydride | 93.5 | 90 | 65 | 80 |
| methacrylic anhydride | 5.5 | 9 | 19 | 10 |
| $C_2H_5-O-\underset{\underset{O}{\parallel}}{C}-O-C_2H_5$ | 1 | 1 | 2 | 2 |
| $C_2H_5-O-\underset{\underset{O}{\parallel}}{C}-O-\underset{\underset{O}{\parallel}}{C}-O-C_2H_5$ | | | 8 | 5 |
| ethyl methacrylate | | | 6 | 3 |
| Yield of carboethoxymethacrylic anhydride relative to the sodium methacrylate | 85.5 | 80 | | |

When the chloroformate/methacrylate molar ratio 20 is less than 1.15, poor selectivity towards carboxyethoxymethacrylic anhydride is observed. It is manifestly impossible to obtain a product of good purity below this molar ratio.

EXAMPLE 10

The process is performed in the same apparatus as in Example 1.

309.3 g of an aqueous 33.5% sodium methacrylate solution stabilized with 0.8 g of hydroquinone methyl ether are loaded in. 192 g of toluene are then introduced, followed by 0.02 mol of tetra-n-butylammonium bromide per mole of sodium methacrylate. 125.1 g of ethyl chloroformate are then introduced with stirring, while controlling the temperature of the medium at 15° C. (ethyl chloroformate/sodium methacrylate molar ratio: 1.2).

The reaction progress is monitored as in Example 3. After reaction for 4 hours, the degree of conversion of the sodium methacrylate is greater than 99%. The phases of the crude product are then separated out by settling but not washed, and stripped of volatiles under vacuum at a temperature of less than 35° C.

The NMR analysis of the product stripped of volatiles is as follows:

| carboethoxymethacrylic anhydride | 95.5% |
|---|---|
| methacrylic anhydride | 4.5% | carboethoxymethacrylic anhydride 95.5%
methacrylic anhydride 4.5%
The yield of carboethoxymethacrylic anhydride is 87.5%.

EXAMPLE 11

Example 6 is repeated, using potassium methacrylate instead of sodium methacrylate and working at 10° C.

The composition of the final product (% by weight) is as follows:

carboethoxymethacrylic anhydride 93%
methacrylic anhydride 6%

| carboethoxymethacrylic anhydride | 93% |
|---|---|
| methacrylic anhydride | 6% |
| $C_2H_5-O-\underset{\underset{O}{\parallel}}{C}-O-C_2H_5$ | 1% |

EXAMPLES 12 TO 14

Example 6 is repeated, working at 10° C. and varying the nature of the phase-transfer catalyst, which is introduced in an amount of 0.01 mol/mole of sodium methacrylate.

TABLE 3

| Example | 12 | 13 | 14 |
|---|---|---|---|
| Phase-transfer catalyst | $(Bu)_4P^{\oplus}Br^{\ominus}$ | $(Bu)_3C_6H_5P^{\oplus}Cl^{\ominus}$ | $(CH_3)(C_8H_{17})_3N^{\oplus}Br^{\ominus}$ |
| Yield of final product (relative to the sodium methacrylate converted) (%) | 94 | 97 | 99.5 |
| Degree of conversion of the sodium methacrylate greater than 98.5% after . . . | 4.5 h | 3 h | 1.5 h |
| Composition of the final product (% by weight) | | | |
| carboethoxymethacrylic anhydride | 94 | 94 | 96 |
| methacrylic anhydride | 4 | 6 | 3 |
| $C_2H_5-O-\underset{\underset{O}{\parallel}}{C}-O-C_2H_5$ | 2 | | 1 |

What is claimed is:

1. A process for manufacturing a high-purity (meth)acrylic anhydride, represented by the general formula (I):

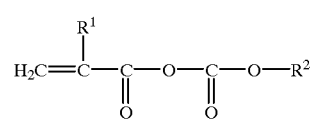

in which:
R¹ represents H or CH₃; and
R² represents an alkyl, alkenyl, aryl, alkaryl or aralkyl residue,
according to which process an alkali metal (meth)acrylate of general formula (II):

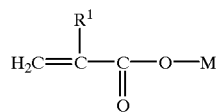

in which:
R¹ is as defined above; and
M is an alkali metal,
is reacted with a chloroformate of general formula (III):

in which R² is as defined above,
characterized in that the said reaction is carried out in an aqueous medium and in the absence of amines, the chloroformate (III)/alkali metal (meth)acrylate (II) molar ratio being at least equal to 1.15.

2. A process according to claim 1, characterized in that the reaction is carried out with compounds (II) and (III) in which:
R² is chosen from $C_1$–$C_{40}$ alkyl, $C_2$–$C_{40}$ alkenyl, phenyl, phenyl ($C_1$–$C_{40}$ alkyl) and ($C_1$–$C_{40}$ alkyl) phenyl residues; and
M represents Na or K.

3. A process according to claim 1, wherein the chloroformate (III)/alkali metal (meth)acrylate (II) molar ratio is between 1.15 and 2.

4. A process according to claim 1, wherein the reaction is carried out at a temperature of between −10 and +30° C.

5. A process according to wherein the alkali metal (meth) acrylate (II) is prepared in aqueous solution by neutralizing (meth)acrylic acid with the hydroxide MOH, the MOH/(meth)acrylic acid molar ratio being between 1 and 1.5 and the water/alkali metal (meth)acrylate (II) weight ratio being between 1.5 and 7, after which the chloroformate (III) is reacted with the alkali metal (meth)acrylate (II).

6. A process according to claim 5, wherein the MOH/(meth)acrylic acid (II) molar ratio is between 1 and 1.1 and the water/alkali metal (meth)acrylate (II) weight ratio is between 1.5 and 2.

7. A process according to wherein the reaction between the alkali metal (meth)acrylate (II) and the chloroformate (III) is carried out in the presence of a phase-transfer catalyst, dissolved or fixed to a polymeric support and used in a proportion of from 0.001 to 0.02 mol, per mole of alkali metal (meth)acrylate (II).

8. A process according to claim 7, wherein the phase-transfer catalyst is chosen from quaternary ammonium salts, phosphonium salts and crow ethers.

9. A process according to claim 1, wherein a multi-phase reaction mixture is formed at the end of the reaction, and further comprising separating the phases by settling at room temperature, and the organic phase containing the mixed anhydride (I) and the excess chloroformate (III) is then stripped of volatiles under vacuum at a temperature of less than or equal to 35° C.

10. A process according to claim 1, wherein at least one polymerization inhibitor is introduced into the reaction medium, in a proportion of from 500 to 5000 ppm, relative to the alkali metal (meth)acrylate (II), or to its precursor (meth)acrylic acid.

11. A process according to claim 10, wherein the polymerization inhibitor is chosen from hydroquinone methyl ether, hydroquinone, phenothiazine and di-tert-butyl-para-cresol.

12. A process according to claim 7, wherein the molar proportion of the catalyst to alkali metal (meth)acrylate (II) is 0.005:1 to 0.01:1, respectively.

13. A process according to claim 9, wherein a separated phase is washed with water at room temperature.

14. A process according to claim 10, wherein the proportion of polymerization inhibitor is 500 to 1000 ppm.

15. A process according to claim 3, wherein said molar ratio is between 1.5 and 1.7.

16. A process according to claim 4, wherein said temperature is between +10 and +20° C.

17. A process according to claim 1, wherein R² is ethyl, n-propyl, isopropyl n-butyl, or isobutyl.

18. A process according to claim 7, wherein said phase-transfer catalyst is $(Bu)_4P^{\oplus}Br^{\ominus}$, $(BU)_3C_6H_5P^{\oplus}Cl^{\ominus}$ or $(CH_3)(C_8H_{17})_3N^{61} Br^{\ominus}$.

19. A process according to claim 18, wherein said phase-transfer catalyst is $(CH_3)(C_8 H_{17})_3N^{\oplus}Br^{\ominus}$.

20. A process according to claim 19, wherein R² is ethyl.

* * * * *

UNITED STATES PATENT AND TRADEMARK OFFICE
CERTIFICATE OF CORRECTION

PATENT NO.     : 6,346,650 B1
DATED          : February 12, 2002
INVENTOR(S)    : Paul et al.

It is certified that error appears in the above-identified patent and that said Letters Patent is hereby corrected as shown below:

<u>Column 10,</u>
Line 43, delete "$N^{61}$" and insert -- $N^{\oplus}$ --.

Signed and Sealed this

Twelfth Day of November, 2002

Attest:

JAMES E. ROGAN
Attesting Officer     Director of the United States Patent and Trademark Office